(12) United States Patent
Zilberman et al.

(10) Patent No.: US 11,974,798 B2
(45) Date of Patent: May 7, 2024

(54) TEMPERATURE-CONTROLLED PULSED RF ABLATION

(71) Applicant: BIOSENSE WEBSTER (ISRAEL) LTD., Yokneam (IL)

(72) Inventors: Israel Zilberman, Yokneam (IL); Assaf Govari, Haifa (IL); Gili Attias, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 944 days.

(21) Appl. No.: 16/037,455

(22) Filed: Jul. 17, 2018

(65) Prior Publication Data

US 2020/0022747 A1    Jan. 23, 2020

(51) Int. Cl.
*A61B 18/12*    (2006.01)
*A61B 18/14*    (2006.01)
*A61B 18/00*    (2006.01)

(52) U.S. Cl.
CPC ...... *A61B 18/1206* (2013.01); *A61B 18/1492* (2013.01); *A61B 2018/00577* (2013.01);
(Continued)

(58) Field of Classification Search
CPC ............ A61B 18/1206; A61B 18/1492; A61B 2018/00577; A61B 2018/00702; A61B 2018/00714; A61B 2018/00791; A61B 2018/00351; A61B 2018/00642; A61B 2018/00666; A61B 2018/00678; A61B 2018/00726; A61B 2018/00761; A61B 2018/00797; A61B 2018/00815; A61B 2018/00821; A61B 2018/00827; A61B 2018/00875; A61B 2090/065; A61B 2218/002
See application file for complete search history.

(56) References Cited

U.S. PATENT DOCUMENTS 6,107,699 A    8/2000    Swanson
6,200,314 B1    3/2001    Sherman
(Continued)

FOREIGN PATENT DOCUMENTS

RU    2013145337 A    4/2015
WO    WO 1996/10950 A1    4/1996

OTHER PUBLICATIONS

European Search Report for corresponding EPA No. 19186545.0 dated Dec. 5, 2019.

*Primary Examiner* — Khadijeh A Vahdat
(74) *Attorney, Agent, or Firm* — Scully, Scott, Murphy & Presser, PC (57) ABSTRACT

Described embodiments include a system that includes a radiofrequency-current (RF-current) generator and a processor. The processor is configured to cause the RF-current generator to generate a plurality of pulses of RF current for application to tissue of a subject, each of the pulses having a power whose maximum value is greater than 80 W and a duration that is less than 10 s, and an intermission between successive ones of the pulses being less than 10 s. The processor is further configured to, while each one of the pulses is applied to the tissue, receive at least one signal that indicates a measured temperature of the tissue, and, in response to the measured temperature, control the power of the pulse. Other embodiments are also described.

16 Claims, 4 Drawing Sheets

(52) U.S. Cl.
CPC ............ *A61B 2018/00666* (2013.01); *A61B 2018/00702* (2013.01); *A61B 2018/00714* (2013.01); *A61B 2018/00761* (2013.01); *A61B 2018/00827* (2013.01)

(56) References Cited

U.S. PATENT DOCUMENTS

| | | |
|---|---|---|
| 6,235,020 B1 | 5/2001 | Cheng |
| 9,072,518 B2 | 7/2015 | Swanson |
| 9,445,725 B2 | 9/2016 | Govari et al. |
| 2002/0151884 A1* | 10/2002 | Hoey .................. A61B 18/14 606/41 |
| 2002/0183638 A1 | 12/2002 | Swanson |
| 2004/0092926 A1 | 5/2004 | Hoey |
| 2008/0045936 A1 | 2/2008 | Vaska |
| 2011/0130648 A1 | 6/2011 | Beeckler et al. |
| 2011/0202058 A1 | 8/2011 | Eder et al. |
| 2012/0203098 A1* | 8/2012 | Raju .................. A61N 7/02 601/3 |
| 2015/0032100 A1* | 1/2015 | Coulson ............ A61B 18/1233 606/35 |
| 2015/0320479 A1 | 11/2015 | Cosman, Jr. |
| 2016/0287312 A1* | 10/2016 | Tegg ................. A61B 18/1492 |
| 2017/0209208 A1 | 7/2017 | Govari et al. |
| 2017/0319260 A1* | 11/2017 | Ngo .................. A61B 18/1206 |

\* cited by examiner

TEMPERATURE-CONTROLLED PULSED RF ABLATION

FIELD OF THE INVENTION

The present invention relates to the field of radiofrequency (RF) ablation, such as for the treatment of cardiac arrhythmias.

BACKGROUND OF THE INVENTION

Radiofrequency (RF) ablation is a treatment modality that kills unwanted tissue by heat. Starting with cardiac arrhythmia treatment in the 1980s, RF ablation has found clinical application in a number of diseases, and is now the treatment of choice for certain types of cardiac arrhythmia, and certain cancers. During RF ablation, an electrode is inserted into proximity with the target region, typically under medical imaging guidance. Subsequently, tissue surrounding the electrode in the target region is destroyed by heating via RF electric current.

U.S. Pat. No. 9,072,518 describes ablation systems and methods that use high-voltage pulses to ablate tissue and form lesions. A variety of different electrophysiology devices, such as catheters, surgical probes, and clamps, may be used to position one or more electrodes at a target location. The electrodes can be connected to power supply lines and, in some instances, the power to the electrodes can be controlled on an electrode-by-electrode basis. High-voltage pulse sequences provide a total amount of heating that is typically less than that which is observed with thermally-based radiofrequency energy ablation protocols.

International Patent Application Publication WO/1996/010950 describes a method for treating ventricular tachycardia that comprises inserting an electrode catheter into the ventricle. The ventricular wall of the heart is contacted with an ablation electrode at a site where an aberrant electrical pathway is located. Radiofrequency is delivered through the ablation electrode to the tissue for a time sufficient to confirm the site of the aberrant electrical pathway and to preheat the tissue. Short high voltage electrical pulses are then delivered to the tissue through the same electrode to thereby form a non-conductive lesion.

US Patent Application Publication 2017/0209208 to Govari et al., whose disclosure is incorporated herein by reference, describes a method, including selecting a first maximum radiofrequency (RF) power to be delivered by an electrode within a range of 70W-100W, and selecting a second maximum RF power to be delivered by the electrode within a range of 20W-60W. The method also includes selecting an allowable force on the electrode within a range of 5 g-50 g, selecting a maximum allowable temperature, of tissue to be ablated, within a range of 55 C-65 C, and selecting an irrigation rate for providing irrigation fluid to the electrode within a range of 8-45 ml/min. The method further includes performing an ablation of tissue using the selected values by initially using the first power, switching to the second power after a predefined time between 3 s and 6 s, and terminating the ablation after a total time for the ablation between 10 s and 20 s.

SUMMARY OF THE INVENTION

There is provided, in accordance with some embodiments of the present invention, a system that includes a radiofrequency-current (RF-current) generator and a processor. The processor is configured to cause the RF-current generator to generate a plurality of pulses of RF current for application to tissue of a subject, each of the pulses having a power whose maximum value is greater than 80 W and a duration that is less than 10 s, and an intermission between successive ones of the pulses being less than 10 s. The processor is further configured to, while each one of the pulses is applied to the tissue, receive at least one signal that indicates a measured temperature of the tissue, and, in response to the measured temperature, control the power of the pulse.

In some embodiments, the processor is configured to drive the RF-current generator to apply fewer than seven pulses.

In some embodiments, the intermission is between 2 and 5 s.

In some embodiments, the duration of each pulse is between 2 and 5 s.

In some embodiments, the processor is configured to drive the RF-current generator to apply each one of the pulses such that the power of the pulse initially rises to, and then plateaus at, the maximum value.

In some embodiments, the maximum value is greater than 100 W.

In some embodiments, the maximum value is greater than 120 W.

In some embodiments, the maximum value is equal to a predefined target power value.

In some embodiments, the processor is configured to control the power of the pulse by alternatingly reducing and increasing the power of the pulse.

In some embodiments, the processor is configured to control the power of the pulse by reducing the power of the pulse in response to the measured temperature approaching a threshold temperature.

In some embodiments, the threshold temperature is between 40° C. and 65° C.

In some embodiments, the threshold temperature is between 40° C. and 55° C.

In some embodiments, during the intermission, no RF energy is applied to the tissue.

There is further provided, in accordance with some embodiments of the present invention, a method that includes generating a plurality of pulses of radiofrequency (RF) current for application to tissue of a subject, each of the pulses having a power whose maximum value is greater than 80 W and a duration that is less than 10 s, and an intermission between successive ones of the pulses being less than 10 s. The method further includes, while each one of the pulses is applied to the tissue, receiving at least one signal that indicates a measured temperature of the tissue, and, in response to the measured temperature, controlling the power of the pulse.

In some embodiments, the tissue includes cardiac tissue of the subject.

The present disclosure will be more fully understood from the following detailed description of the embodiments thereof, taken together with the drawings, in which:

DETAILED DESCRIPTION OF EMBODIMENTS

Overview

Radiofrequency (RF) ablation in prior art systems is typically performed at continuous power levels of the order of 20-50 watts, with a contact force of approximately 10 g, and under irrigation, for a duration of approximately one minute. Such a protocol generally provides for a lesion depth on the order of 5 mm. To achieve a greater depth, such as 6-10 mm, it is typically necessary to increase the duration over which the RF current is applied, or to increase the power level of the current. However, both of these options may be undesirable, e.g., due to the possibility of steam pops forming within the tissue.

To address this challenge, US Patent Application Publication 2017/0209208 describes a range of values of contact force and irrigation rate that facilitates the application of continuous power of approximately 100 watts. During the ablation procedure, the temperature of the tissue being ablated is carefully monitored and recorded at a high rate. If the monitored temperature exceeds a preset maximum temperature limit, the RF power supplied to the tissue is reduced. Alternatively or additionally, the impedance to the RF energy supplied to the tissue may be monitored, and if the impedance increases by more than a preset value, the RF energy supply may be halted. The high power of the RF current facilitates shortening the duration of the RF current to much less than one minute. Additionally, due to the monitoring of the tissue temperature and/or impedance, there is little risk of any steam pops being formed.

Embodiments of the present invention further increase the efficacy and safety of the ablation procedure, by applying the RF energy in multiple short, high-power pulses, typically of 100 W or greater, instead of in a continuous current. The break following each pulse allows the tissue to cool, such that the subsequent pulse may again be applied at high power. During each pulse, the temperature of the tissue may be monitored as described above, and the amplitude of the pulse may be adjusted responsively thereto. Advantageously, this protocol facilitates quickly and safely attaining relatively large lesion depths.

System Description

Figure 1:
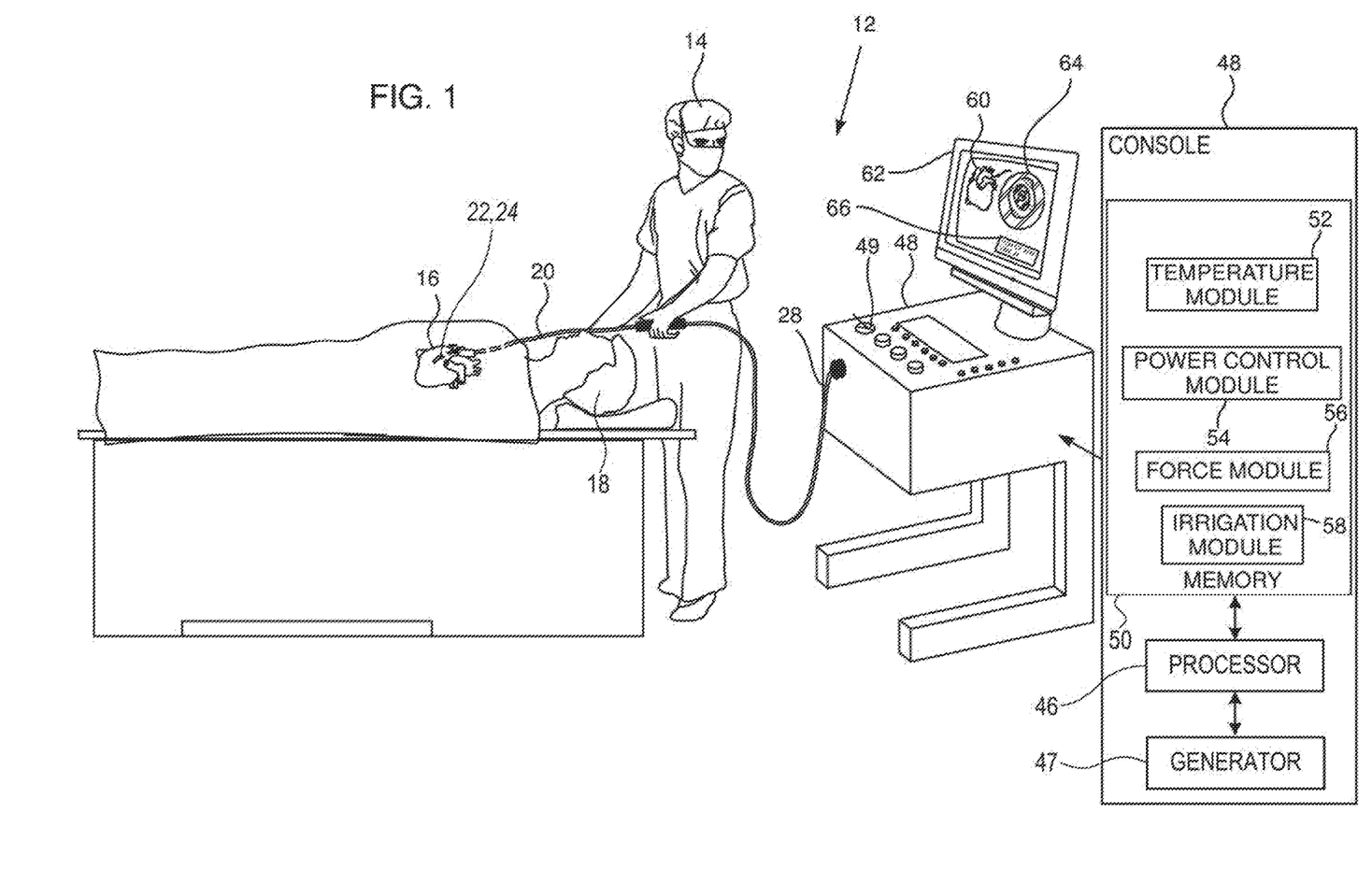
FIG. 1 is a schematic illustration of an ablation system used to perform an ablation procedure, according to an embodiment of the present invention.

Reference is initially made to FIG. 1, which is a schematic illustration of an ablation system 12 used to perform an ablation procedure, according to an embodiment of the present invention. By way of example, this procedure is assumed to comprise ablation of a portion of a myocardium of the heart 16 of a human patient 18. However, it will be understood that embodiments of the present invention may be similarly applied to any ablation procedure on biological tissue.

To perform the ablation, physician 14 inserts a probe 20 into a lumen of patient 18, so that a distal end 22 of probe 20 enters heart 16 of the patient. Distal end 22, which is described in more detail below with reference to FIGS. 2A-D, comprises one or more electrodes 24, which are caused by the physician to contact respective locations of the myocardium. Probe 20 further comprises a proximal end 28, which is connected, via a suitable electrical interface such as a port or socket, to an operating console 48.

System 12 is controlled by a system processor 46, which is typically located in operating console 48. In general, processor 46 may be embodied as a single processor, or as a cooperatively networked or clustered set of processors. Processor 46 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

During the procedure, processor 46 typically tracks the location and orientation of distal end 22 of the probe, using any suitable method known in the art. For example, processor 46 may use a magnetic tracking method, wherein magnetic transmitters external to patient 18 generate signals in coils positioned in the distal end of the probe. The Carto® system, produced by Biosense Webster, uses such a tracking method. The track of distal end 22 is typically displayed on a three-dimensional representation 60 of the heart of patient 18, on a screen 62. The progress of the ablation procedure is typically also displayed on screen 62, as a graphic 64 and/or alphanumeric data 66.

To control the relevant components of system 12, processor 46 may load, and execute, relevant software modules stored in a memory 50. Typically, memory 50 stores a temperature module 52, a power control module 54, a force module 56, and an irrigation module 58, the respective functions of which are described below. (In general, any relevant processing function described below may be said to be performed either by the processor, or by the module that is executed by the processor to perform the function.)

Console 48 comprises an RF-current generator 47, configured to generate the RF currents used for the ablation procedure. Console 48 further comprises controls 49, which are used by physician 14 to communicate with processor 46. Console 48 may further comprise any other suitable hardware or software elements, to facilitate communication between processor 46 and probe 20.

Figure 2A:
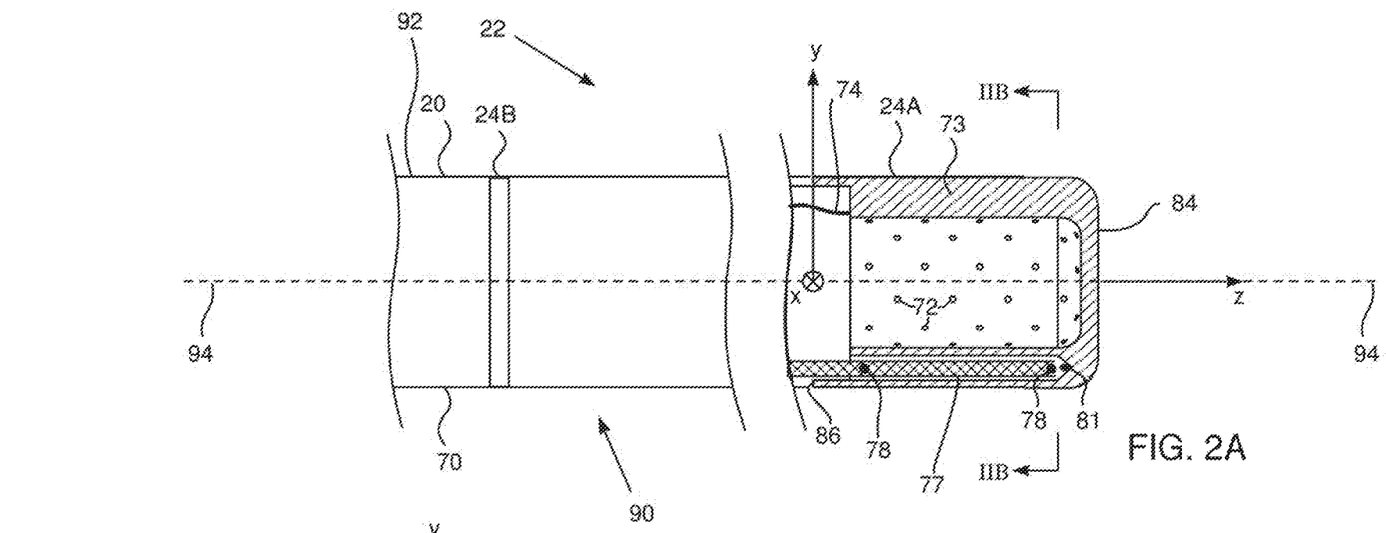
FIGS. 2A, 2B, 2C, and 2D schematically illustrate a distal end of a probe used in the system, according to an embodiment of the present invention.
Figure 2B:
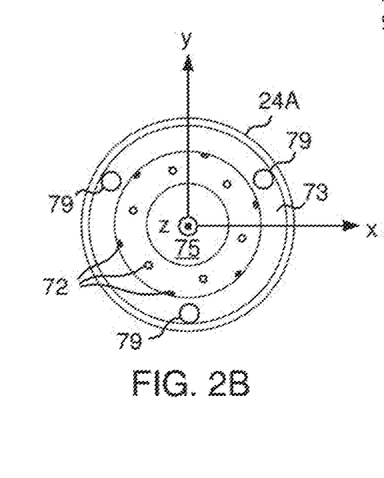
Figure 2C:
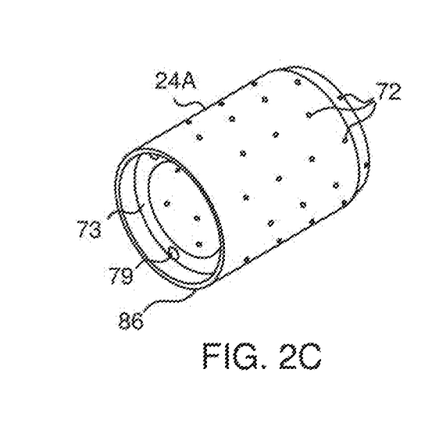
Figure 2D:
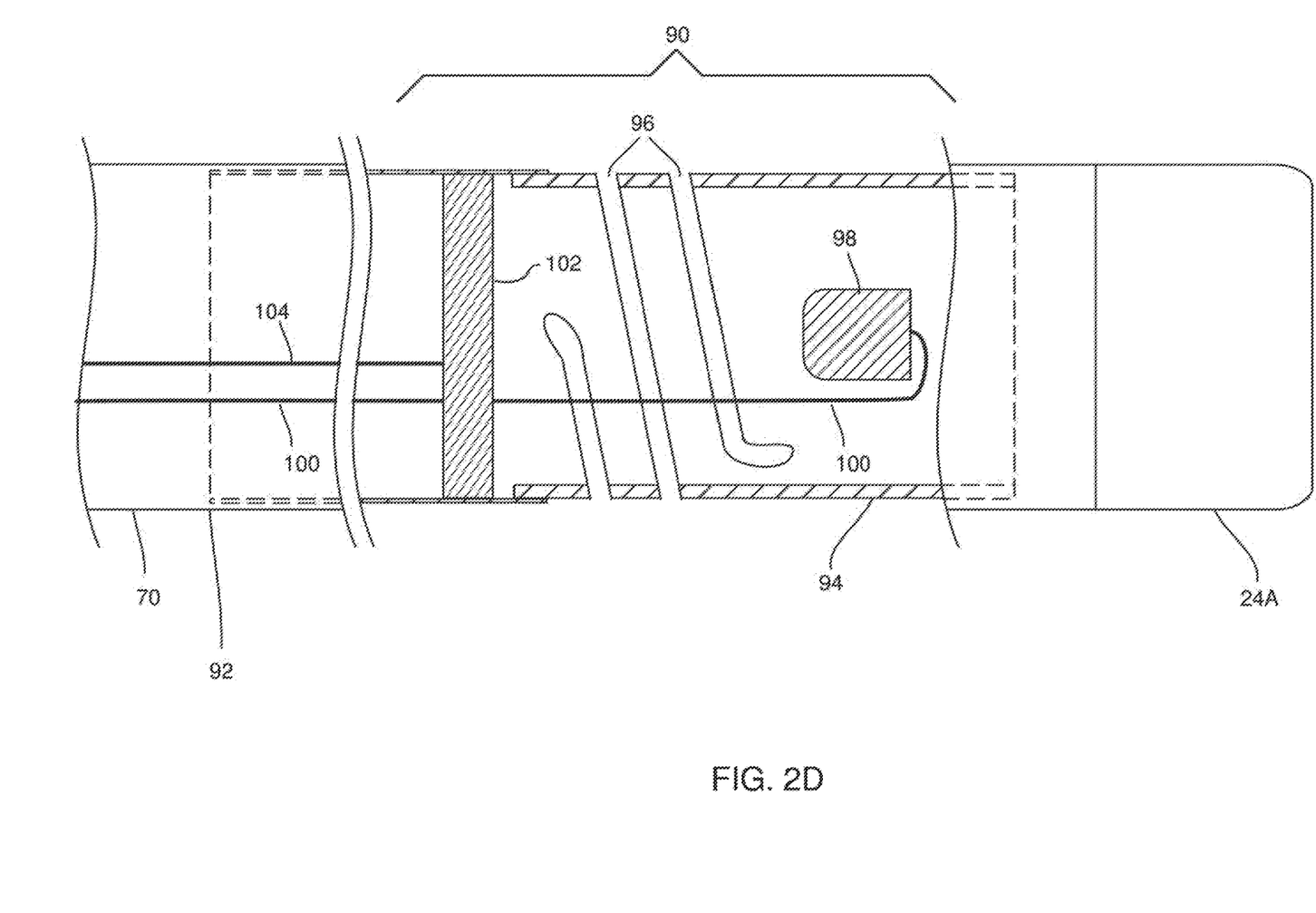

Reference is now made to FIGS. 2A-D, which schematically illustrate distal end 22 of probe 20, according to an embodiment of the present invention. FIG. 2A is a sectional view along the length of the probe, FIG. 2B is a cross-sectional view along a cut IIB-IIB that is marked in FIG. 2A, FIG. 2C is a perspective view of a section of the distal end, and FIG. 2D is a schematic cross-sectional view of a force sensor 90 incorporated into a proximal portion 92 of the distal end.

As shown in FIG. 2A, an insertion tube 70 extends along the length of the probe and is connected at the termination of its distal end to a conductive cap electrode 24A, which is used for ablation. (Conductive cap electrode 24A is herein also termed an "ablation electrode," or simply a "cap.") Cap electrode 24A has an approximately plane conducting surface 84 at its distal end, and a substantially circular edge 86 at its proximal end. Proximal to ablation electrode 24A, there are typically other electrodes, such as a ring electrode 24B. Typically, insertion tube 70 comprises a flexible, biocompatible polymer, while electrodes 24A and 24B comprise a biocompatible metal, such as gold or platinum, for example. Ablation electrode 24A is typically perforated by an array of irrigation apertures 72. In one embodiment, there are 36 apertures 72, distributed evenly over electrode 24A.

An electrical conductor 74 conveys radiofrequency (RF) electrical energy from console 48 (FIG. 1), through insertion tube 70, to electrode 24A, and thus energizes the electrode to ablate myocardial tissue with which the electrode is in contact. As described below, power control module 54 controls the level of RF power dissipated via electrode 24A. During the ablation procedure, irrigation fluid flowing out through apertures 72 irrigates the tissue under treatment, and the rate of flow of fluid is controlled by irrigation module 58. The irrigation fluid is delivered to electrode 24A by a tube (not shown in the diagram) within insertion tube 70.

Temperature sensors 78 are mounted within conductive cap electrode 24A at locations that are arrayed around the distal tip of the probe, both axially and circumferentially. In a disclosed embodiment considered herein, cap 24A contains six such sensors, with one group of three sensors in a distal location, close to the tip, and another group of three sensors in a slightly more proximal location. This distribution is shown only by way of example, however, and greater or smaller numbers of sensors may be mounted in any suitable locations within the cap. Sensors 78 may comprise thermocouples, thermistors, or any other suitable type of miniature temperature sensor. Sensors 78 are connected by leads (not shown in the diagram) running through the length of insertion tube 70. Temperature signals are thus carried, over the leads, to temperature module 52.

In a disclosed embodiment, cap 24A comprises a side wall 73 that is relatively thick, on the order of 0.5 mm thick, in order to provide the desired thermal insulation between temperature sensors 78 and the irrigation fluid inside a central cavity 75 of the tip. The irrigation fluid exits cavity 75 through apertures 72. Sensors 78 are mounted on rods 77, which are fitted into longitudinal bores 79 in side wall 73. Rods 77 may comprise a suitable plastic material, such as polyimide, and may be held in place at their distal ends by a suitable glue 81, such as epoxy. U.S. Pat. No. 9,445,725, which is incorporated herein by reference, describes a catheter having temperature sensors mounted in a similar configuration to that described above.

The arrangement described above provides an array of six sensors 78, but other arrangements, and other numbers of sensors, will be apparent to those having ordinary skill in the art, and all such arrangements and numbers are included within the scope of the present invention.

In the description herein, distal end 22 is assumed to define a set of xyz orthogonal axes, where an axis 95 of the distal end corresponds to the z axis of the set. For simplicity and by way of example, the y axis is assumed to be in the plane of the paper, the xy plane is herein assumed to correspond to the plane defined by edge 86, and the origin of the xyz axes is assumed to be the center of the circle.

FIG. 2D is a schematic, sectional view of force sensor 90, according to an embodiment of the present invention. Sensor 90 comprises a spring 94, herein assumed to comprise a plurality of helices 96, connecting cap 24A to proximal portion 92. A position sensor 98 is fixed to the distal side of spring 94, and is herein assumed to comprise one or more coils coupled by conductors 100 to force module 56.

An RF transmitter 102, typically a coil, is fixed to the proximal side of spring 94, and the RF energy for transmitter 102 is provided from console 48, under the control of force module 56, via conductors 104. The RF energy from the transmitter traverses sensor 98, generating a corresponding signal in conductors 100 of the sensor.

In operation, as force is exerted on cap 24A, sensor 98 moves relative to transmitter 102, and the movement causes a change in the signals of the sensor. Force module 56 uses the change in signal of the sensor to provide a metric of the force on cap 24A. The metric typically provides the force in magnitude and direction.

A more detailed description of a sensor similar to sensor 90 is provided in US Patent Application 2011/0130648, which is incorporated herein by reference.

Returning to FIG. 1, temperature module 52 receives signals from the six temperature sensors 78 within cap 24A, and uses the signals to determine a maximum value of the six measured temperatures. The temperature module is typically configured to calculate the maximum temperature at a fixed rate, such as every 20-40 ms, for example. In some embodiments, the maximum temperature is determined at a frequency of at least 30 Hz. The calculated maximum temperature is herein also termed the measured temperature, and the measured temperature is registered as the temperature of the tissue being ablated. The temperature module passes the measured temperature value to power control module 54, such that the power control module may control the RF current responsively to the measured temperature.

Power control module 54 may provide RF power to cap 24A in any suitable range, such as a range of 1W to 130W, 140W, or 150W. The power control module also measures the impedance of cap 24A, i.e., the impedance to the RF current passed from cap 24A. The impedance is typically measured at a predefined rate, such as every 400-600 ms, for example. If the impedance increases from a previous impedance measurement by more than a preset value, such as 7Ω, the power control module may stop the RF delivery to cap 24A, since an increase of impedance may indicate an unwanted change in the tissue being ablated, such as charring or steam popping.

Typically, prior to the ablation procedure, the physician defines an RF-pulse profile, by selecting relevant parameters such as a number of pulses, a maximum (or "target") power for each pulse, the duration of each pulse, and the time between successive pulses. The power control module then causes RF generator 47 to generate a plurality of pulses of RF current for application to the subject's tissue, in accordance with the defined profile. Each of these pulses is supplied by the generator to probe 20. While the probe applies the pulse, the power control module controls the power of the pulse responsively to the measured temperature received from temperature module 52, as further described below with reference to FIG. 3. For example, the power control module may reduce the power delivered responsively to the measured temperature approaching a threshold temperature that is set by physician 14, such as to reduce the chance of undesirable effects such as charring, coagulation on cap 24A, and/or steam pops in the tissue being ablated.

Typically, during the ablation session, processor 46 causes screen 62 to display the values of the parameters selected by the physician. Processor 46 may also cause screen 62 to display to the physician, by methods known in the art, the progress of the RF delivery. The display of the progress may be graphical, such as a simulation of the dimensions of the lesion as it is produced by the ablation, and/or alphanumeric.

As explained above, force module 56 measures the force on cap 24A. In an embodiment, the allowable force for an ablation is in the range of 5 g-35 g. Similarly, irrigation module 58 governs the rate at which irrigation fluid is delivered to the probe tip. In some embodiments of the present invention, this rate may be set within the range of 8-45 ml/min.

Pulsed RF Ablation

As described above in the Overview and with reference to FIG. 1, embodiments described herein provide for the safe application of short, high-powered pulses of RF current to the subject's tissue (e.g., cardiac tissue), such as to achieve a relatively deep lesion in a relatively short amount of time. In this regard, reference is now made to FIG. 3, which is a schematic illustration of an application of pulsed RF ablation, in accordance with some embodiments of the present invention.

Figure 3:
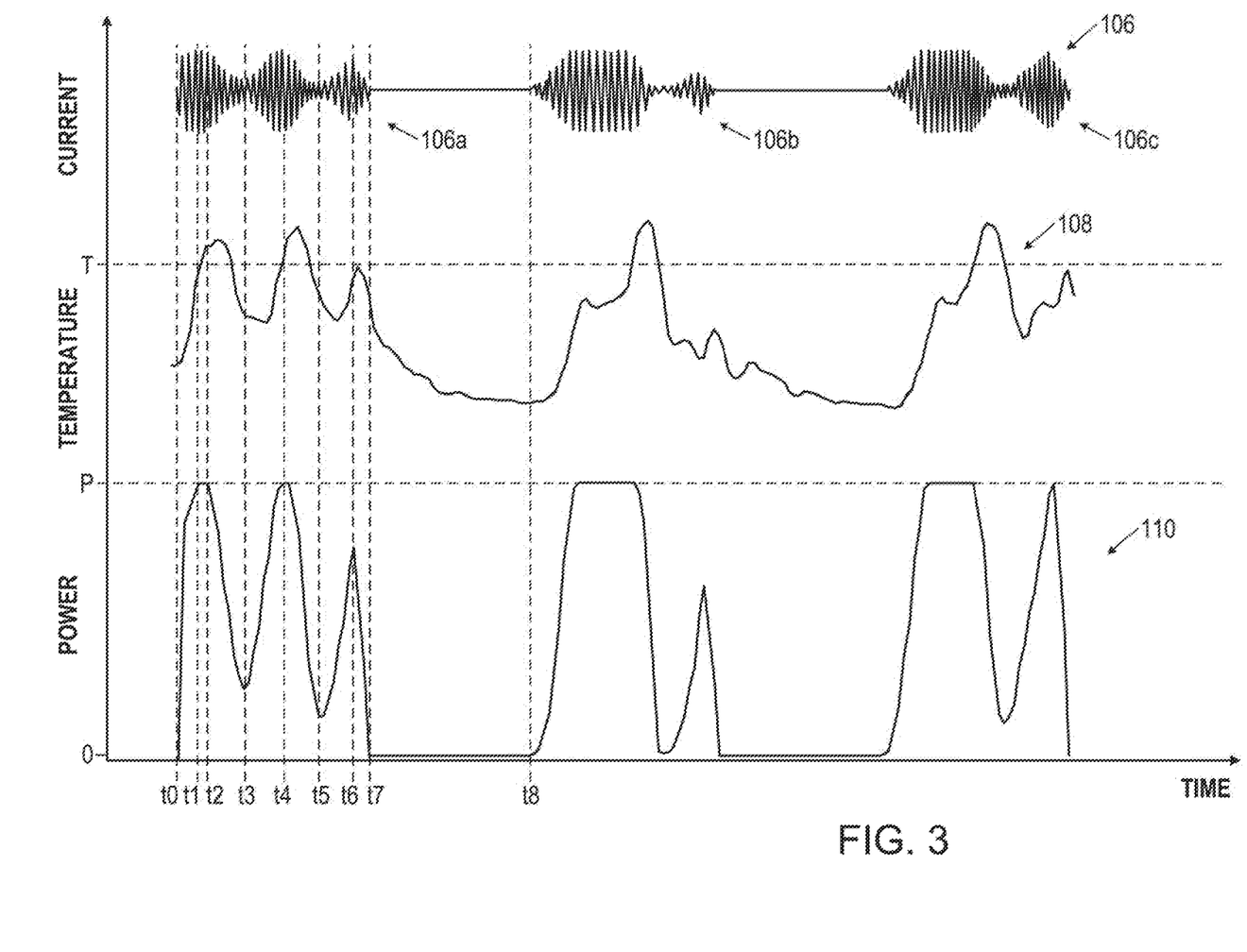
FIG. 3 is a schematic illustration of an application of pulsed RF ablation, in accordance with some embodiments of the present invention.

FIG. 3 shows a plurality of RF current pulses 106, comprising a first pulse 106a, a second pulse 106b, and a third pulse 106c. Pulses 106 are applied by processor 46 to the tissue of patient 18, using RF generator 47 and probe 20.

FIG. 3 further shows the temperature 108 at the interface between the tissue and probe 20, as measured during the application of pulses 106. Temperature 108, which may be more succinctly described as "the temperature of the tissue," may be computed by temperature module 52 by taking the maximum of the individual measurements received from temperature sensors 78, as described above with reference to FIG. 1.

FIG. 3 further shows the power 110 of pulses 106. As described in detail below, the amplitude—and hence, power—of each pulse 106 is controlled by processor 46, in response to measured temperature 108.

Pulses 106, temperature 108, and power 110 are plotted along a common time axis, with particular times of significance t0 . . . t8 being marked. Although the data in FIG. 3 are based on the results of an actual experimental procedure that was carried out, specific numerical values are omitted from FIG. 3, for the sake of generality.

Typically, each pulse 106 has a power whose maximum value is greater than 80 W, such as greater than 100 W or 120 W. (In other words, the power of each pulse may, for at least one instant during the application of the pulse, exceed 80 W, 100 W, or 120 W.) Typically, the duration of each pulse is less than 10 s; for example, the duration of the pulse may be between 2 and 5 s. Thus, for example, the duration between time t0, the time at which first pulse 106a begins, and time t7, the time at which the first pulse ends, may be between 2 and 5 s.

Each pair of successive pulses is separated by an intermission, during which, typically, no energy is applied to the tissue. Typically, the intermission is less than 10 s, such as between 2 and 5 s. For example, the duration between time t7 and time t8, the time at which the second pulse begins, may be between 2 and 5 s. As described above in the Overview, the intermissions facilitate the cooling of the tissue between the applications of the pulses.

Typically, each one of the pulses is applied such that the power of the pulse initially rises to, and then plateaus at, the aforementioned maximum power value. Typically, this maximum value is equal to a predefined target power value P, which, as described above, may be greater than 80 W, 100 W, or 120 W. Following this initial plateau, the power of the pulse typically oscillates as the pulse is controlled responsively to the measured temperature of the tissue, as described in further detail immediately below.

While each pulse is applied, processor 46 controls the power of the pulse in response to measured temperature 108. For example, the processor may reduce the power of the pulse, in response to the measured temperature approaching, reaching, or exceeding a threshold temperature T, which may, for example, be between 40° C. and 65° C., such as between 40° C. and 55° C. Similarly, the processor may increase the power of the pulse, in response to the measured temperature being sufficiently less than T. Thus, typically, the processor alternatingly reduces and increases the power of each pulse, responsively to temperature 108.

In some embodiments, to control each pulse, the processor continually uses the temperature reading to compute a required fractional change in power, and then adjusts the power of the pulse by this required change. For example, as described in US Patent change may be the minimum of $$\frac{a(T_{t-1} - T_t)}{T} + \frac{b(T - T_t)}{T} \text{ and } \frac{(P - P_t)}{P},$$

where $T_t$ is the current measured temperature, $T_{t-1}$ is the previous measured temperature, $P_t$ is the current power of the pulse, and a and b are constants. (In one embodiment, for example, a=10 and b=1.)

FIG. 3 demonstrates the use of the above-described control technique. In particular, the power of the first pulse rises from time t0, until the target power is reached at time t1. Subsequently, the power does not increase further, due to the null value of $$\frac{(P - P_t)}{P}.$$

At time t2, temperature 108 is sufficiently close to T, such that $$\frac{a(T_{t-1} - T_t)}{T} + \frac{b(T - T_t)}{T}$$

is negative, and the power is accordingly decreased. The power continues to be decreased until time t3. At time t3, the temperature has dropped sufficiently such that the computed required power change is again positive, and so the power is again increased, until the target power is again reached at time t4. Subsequently, the power briefly plateaus for a second time, before again decreasing, due to the high temperature. At time t5, the power is again increased. Finally, at time t6, the processor rapidly reduces the power to zero, in order that the duration of the pulse does not exceed the predefined pulse duration. A similar oscillation in power 110 may be observed for the second and third pulses.

In general, the ablation procedure may include the application of any number of pulses that is greater than one. Typically, however, the desired lesion depth may be reached with fewer than seven pulses, such that fewer than seven (e.g., fewer than six) pulses are applied. During each pulse, power 110 may reach the target power P any number of times.

Typically, while each pulse is applied, the processor measures the impedance to the pulse, as described above with reference to FIG. 1. As further described above, in response to a significant increase in this measured impedance, the processor may halt the application of the RF current.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A system for pulsed RF ablation, comprising:
a radiofrequency-current (RF-current) generator configured to generate RF-current to ablate tissue;
an electrode operatively connected to the RF-current generator; and
a processor, configured to:
cause the RF-current generator to generate a plurality of pulses of RF current for application to tissue of a subject for cardiac ablation, wherein the processor is configured to drive the RF-current generator to apply each one of the pulses such that power of the pulse initially rises from zero to a maximum value, wherein the RF-current generator is configured to generate pulses each having a duration from a start point in time to an end point in time greater than zero and less than 10 seconds, and an intermission between the end point and the start point of successive pulses being greater than zero and less than 10 seconds for cooling the tissue, and
while each one of the pulses is applied to the tissue, receive at least one signal from a temperature measuring device operatively connected to the processor, the temperature measuring device configured to measure a temperature of the tissue being ablated, and, in response to the measured temperature, control the power of the pulse through a power control module, the power control module configured to fractionally change the power of each of the pulses between the start point and end point in response to the measured temperature by alternatingly fractionally reducing and fractionally increasing the power of the pulse, an amount of the fractional increase and decrease varying between zero and the maximum value in accordance with a calculation based on a predefined function of the temperature of the tissue being ablated.

2. The system according to claim 1, wherein the maximum value is equal to a predefined target power value.

3. The system according to claim 1, wherein the processor is configured to control the power of the pulse by fractionally reducing the power of the pulse in response to the measured temperature approaching a threshold temperature.

4. The system according to claim 3, wherein the measured temperature approaches the threshold temperature when the measured temperature causes the calculated fractional change to be negative.

5. The system according to claim 1, wherein the processor is configured to fractionally increase the power of the pulse when the measured temperature causes the calculated fractional change to be positive.

6. The system according to claim 1, wherein the processor is configured to fractionally decrease the power of the pulse when the measured temperature causes the calculated fractional change to be negative.

7. The system according to claim 1, wherein the RF-current generator is configured to generate pulses according to an RF pulse profile and wherein the RF pulse profile is modified by the calculated amount of fractional change to the power of the pulses.

8. The system according to claim 1, wherein predefined function of temperature comprises a threshold temperature, a currently measured temperature, and a previously measured temperature.

9. The system according to claim 8, wherein the fractional change is a minimum of the power change calculated as function of temperature and a power change calculated as a function of power, the function of power comprising a target power and a currently measured power of the pulse.

10. A method for pulsed RF ablation, comprising:
generating a plurality of pulses of radiofrequency (RF) current for application to tissue of a subject with a radiofrequency-current (RF-current) generator for cardiac ablation, driving the RF-current generator to apply each one of the pulses such that power of the pulse initially rises from zero to a maximum value, wherein the RF-current generator is configured to generate pulses each having a duration from a start point in time to an end point in time greater than zero and less than 10 seconds, and an intermission between successive pulses of greater than zero and less than 10 seconds for cooling the tissue;
applying the pulses to the tissue through an electrode in contacting relation to the tissue and operatively connected to the RF-current generator; and
while each one of the pulses is applied to the tissue, receiving at least one signal that indicates a measured temperature of the tissue from a temperature sensing device, and, in response to the measured temperature, controlling the power of the pulse through a power control module, the power control module configured to fractionally change the power of each of the pulses between the start point and end point in response to the measured temperature by alternatingly fractionally reducing and fractionally increasing the power of the pulse, an amount of fractional increase and decrease varying between zero and the maximum value according to a calculation based on a predefined function of the temperature of the tissue being ablated.

11. The method according to claim 10, wherein the measured temperature approaches a threshold temperature when the measured temperature causes the calculated fractional change to be negative.

12. The method according to claim 10, wherein the power of the pulse is fractionally increased when the measured temperature causes the calculated fractional change to be positive.

13. The method according to claim 10, wherein power of the pulse is fractionally decreased when the measured temperature causes the calculated fractional change to be negative.

14. The method according to claim 10, wherein the RF-current generator is configured to generate pulses according to an RF pulse profile and wherein the RF pulse profile is modified by the calculated amount of fractional change to the power of the pulses.

15. The method according to claim 10, wherein predefined function of temperature comprises a threshold temperature, a currently measured temperature, and a previously measured temperature.

16. The method according to claim 15, wherein the fractional change is a minimum of the power change calculated as function of temperature and a power change calculated as a function of power, the function of power comprising a target power and a currently measured power of the pulse.

* * * * *